(12) United States Patent
Kreutzer et al.

(10) Patent No.: US 8,877,726 B2
(45) Date of Patent: *Nov. 4, 2014

(54) METHOD AND MEDICAMENT FOR INHIBITING THE EXPRESSION OF A GIVEN GENE

(71) Applicant: Alnylam Pharmaceuticals, Inc., Cambridge, MA (US)

(72) Inventors: Roland Kreutzer, Weidenberg (DE); Stefan Limmer, Kulmbach (DE)

(73) Assignee: Alnylam Pharmaceuticals, Inc., Cambridge, MA (US)

(*) Notice: Subject to any disclaimer, the term of this patent is extended or adjusted under 35 U.S.C. 154(b) by 139 days.

This patent is subject to a terminal disclaimer.

(21) Appl. No.: 13/656,513

(22) Filed: Oct. 19, 2012

(65) Prior Publication Data

US 2014/0051166 A1    Feb. 20, 2014

Related U.S. Application Data

(60) Continuation of application No. 11/982,325, filed on Oct. 31, 2007, now abandoned, which is a continuation of application No. 10/612,179, filed on Jul. 2, 2003, now Pat. No. 8,202,980, which is a division of application No. 09/889,802, filed as application No. PCT/DE00/00244 on Jan. 29, 2000, now abandoned.

(30) Foreign Application Priority Data

Jan. 30, 1999  (DE) .................................. 199 03 713
Nov. 24, 1999  (DE) .................................. 199 56 568

(51) Int. Cl.
| | | |
|---|---|---|
| C12N 15/113 | (2010.01) | |
| A61K 31/713 | (2006.01) | |
| C12N 15/11 | (2006.01) | |
| A61K 38/00 | (2006.01) | |

(52) U.S. Cl.
CPC ............ *C12N 15/113* (2013.01); *A61K 31/713* (2013.01); *C12N 15/111* (2013.01); *A61K 38/00* (2013.01); *C12N 2310/111* (2013.01); *C12N 2310/14* (2013.01); *C12N 2310/53* (2013.01); *C12N 2330/30* (2013.01)
USPC ...................................................... 514/44 A

(58) Field of Classification Search
None
See application file for complete search history.

(56) References Cited

U.S. PATENT DOCUMENTS

| | | | |
|---|---|---|---|
| 5,683,873 A | 11/1997 | George et al. | |
| 5,739,271 A | 4/1998 | Sridhar et al. | |
| 6,107,094 A | 8/2000 | Crooke | |
| 6,506,559 B1 | 1/2003 | Driver et al. | |
| 7,196,184 B2 | 3/2007 | Heidenreich et al. | |
| 7,198,814 B2 | 4/2007 | Endo et al. | |
| 7,348,314 B2 | 3/2008 | John et al. | |
| 7,473,525 B2 | 1/2009 | Kreutzer et al. | |
| 7,745,418 B2 | 6/2010 | John et al. | |
| 7,763,590 B2 | 7/2010 | Kreutzer et al. | |
| 7,829,693 B2 | 11/2010 | Kreutzer et al. | |
| 7,846,907 B2 | 12/2010 | Heidenreich et al. | |
| 7,994,309 B2 | 8/2011 | Kreutzer et al. | |
| 8,101,584 B2 | 1/2012 | Kreutzer et al. | |
| 8,101,742 B2 | 1/2012 | Kreutzer et al. | |
| 8,114,851 B2 | 2/2012 | Kreutzer et al. | |
| 8,114,981 B2 | 2/2012 | Kreutzer et al. | |
| 8,119,608 B2 | 2/2012 | Kreutzer et al. | |
| 8,168,776 B2 | 5/2012 | Kreutzer et al. | |
| 8,183,362 B2 | 5/2012 | Kreutzer et al. | |
| 8,202,980 B2 | 6/2012 | Kreutzer et al. | |
| 8,273,868 B2 | 9/2012 | John et al. | |
| 8,273,870 B2 | 9/2012 | Kreutzer et al. | |
| 8,546,143 B2 | 10/2013 | Kreutzer et al. | |
| 2003/0134808 A1 | 7/2003 | Wengel | |

OTHER PUBLICATIONS

Response to Summons to Attend Oral Proceedings pursuant to Rule 115(1) issued on Oct. 12, 2012, filed by Patentee Alnylam Europe AG on Jan. 7, 2013, for European Patent Application No. EP 02003683.6/ EP 1214945, 27 Pages.

Office Action for U.S. Appl. No. 13/753,438, mailed Jan. 29, 2013, 15 Pages.

Office Action for U.S. Appl. No. 11/982,325, mailed Jul. 10, 2013, 11 Pages.

Office Action for U.S. Appl. No. 11/982,345 mailed Jul. 29, 2013, 6 Pages.

Notice of Reasons for Rejection for Japanese Patent Application No. JP 2009-285705, Jul. 17, 2012, 13 Pages.

Notice of Reasons for Rejection for Japanese Patent Application No. JP 2009-285706, Jul. 17, 2012, 10 Pages.

Summons to oral proceedings pursuant to Rule 115 (1) EPC, European Patent Appl. No. EP 02003683, Jul. 23, 2012, 28 Pages.

Statutory Declaration A by Fiona H. Cameron, Opposition by Sirna Therapeutics against Australian Patent Application No. AU 2005201044, Nov. 20, 2012, 33 Pages.

Statutory Declaration A by Fiona H. Cameron, Opposition by Sirna Therapeutics against Australian Patent Application No. AU 2005201044, Nov. 20, 2012, 13 Pages.

Beigelman, L., et al., "Synthesis of 2'-modified nucleotides and their incorporation into hammerhead ribozymes," Nucleic Acids Research, 1995, pp. 4434-4442, vol. 23, No. 21.

Cameron, F.H., et al., "Specific gene suppression by engineered ribozymes in monkey cells," Proc. Natl. Acad. Sci., Biochemistry, Dec. 1989, pp. 9139-9143, vol. 86.

(Continued)

*Primary Examiner* — Tracy Vivlemore
(74) *Attorney, Agent, or Firm* — Fenwick & West LLP

(57) ABSTRACT

The invention relates to an isolated RNA that mediates RNA interference of an mRNA to which it corresponds and a method of mediating RNA interference of mRNA of a gene in a cell or organism using the isolated RNA.

18 Claims, 5 Drawing Sheets

(56) References Cited

OTHER PUBLICATIONS

Figure 1:
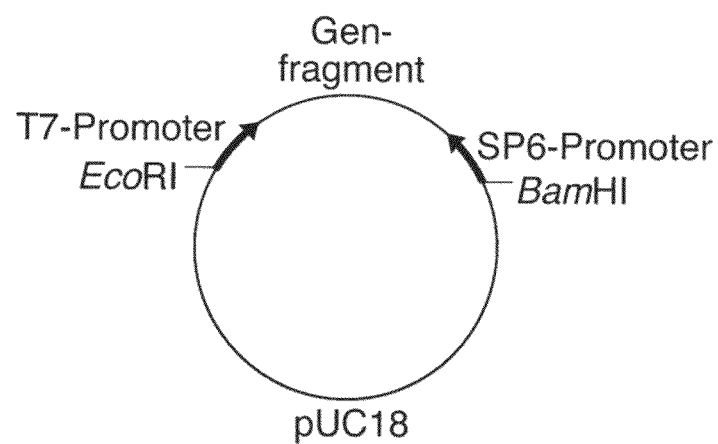

Dropulic, B., et al., "Functional Characterization of a U5 Ribozyme: Intracellular Suppression of Human Immunodeficiency Virus Type 1 Expression," Journal of Virology, Mar. 1992, pp. 1432-1441, vol. 66, No. 3.

Fakler, B., et al., "Short Antisense Oligonucleotide-mediated Inhibition Is Strongly Dependent on Oligo Length and Concentration but Almost Independent of Location of the Target Sequence," The Journal of Biological Chemistry, Jun. 10, 1994, pp. 16187-16194, vol. 269, No. 23.

Hendry, P., et al., "Redesigned and chemically-modified hammerhead ribozymes with improved activity and serum stability," BMC Chemical Biology, Dec. 9, 2004, pp. 1-11, vol. 4, No. 1.

Inouye, M., Antisense RNA: Its functions and applications in gene regulation—a review Gene, 1988, pp. 25-34, vol. 72.

Kuss, B., et al., "Antisense—time to shoot the messenger," Annals of Oncology, 1999, pp. 495-503, vol. 10.

Lesnik, E., et al., "Oligodeoxynucleotides Containing 2'-O-Modified Adenosine: Sythesis and Effects on Stability of DNA:RNA Duplexes," Biochemistry, 1993, pp. 7832-7838, vol. 32.

Loke, S. L., et al., "Characterization of oligonucleotide transport into living cells," Proc. Natl. Acad. Sci., Biochemistry, May 1989, pp. 3474-3478, vol. 86.

McCall, M., et al., "Minimized Hammerhead Ribozymes," Methods in Molecular Biology, 1997, pp. 151-159, vol. 74.

Summerton, J., et al., "Morpholino Antisense Oligomers: Design, Preparation, and Properties," Antisense & Nucleic Acid Drug Development, 1997, pp. 187-195, vol. 7.

Shibahara, S., et al., "Inhibition of human immunodeficiency virus (HIV-1) replication by synthetic oligo-RNA derivatives," Nucleic Acids Research, 1989, pp. 239-252, vol. 17, No. 1.

Tachibana, R., et al., "Quantitative Analysis of Correlation between Number of Nuclear Plasmids and Gene Expression Activity after Transfection with Cationic Liposomes," Pharmaceutical Research, Apr. 2002, pp. 337-381, Apr. 2002, vol. 19, No. 4.

Van Der Krol, A., et al., "An anti-sense chalcone synthase gene in transgenic plants inhibits fewer pigmentation," Nature, Jun. 30, 1988, pp. 866-869, vol. 333.

Wikipedia, "File: NIH 3T3.jpg," NIH/3T3 Mouth Embry Fibroblast, May 9, 2007, 1 page, can be retrieved at //commons.wikimedia.org/wiki/File:NIH_3T3.jpg.

Wang, L., et al., "Preclinical Characterization of an Anti-tat Ribozyme for Therapeutic Application," Human Gene Therapy, Jun. 10, 1998, pp. 128-1291, vol. 9.

Office Action for U.S. Appl. No. 13/656,540, mailed Nov. 22, 2013, 13 Pages.

Office Action for U.S. Appl. No. 13/656,548, mailed Dec. 17, 2013, 14 Pages.

Notice in accordance with article 94 (3) EPC for European Patent Application No. EP 06025389.5, Oct. 8, 2013, 10 pages.

Notice in accordance with article 94 (3) EPC for European Patent Application No. EP 10011217.6, Oct. 9, 2013, 11 pages.

Office Action for U.S. Appl. No. 13/753,438, Apr. 26, 2013, 14 Pages.

SEQUENCE LISTING

```
<160> NUMBER OF SEQ ID NOS: 8

<210> SEQ ID NO 1
<211> LENGTH: 45
<212> TYPE: DNA
<213> ORGANISM: Artificial Sequence
<220> FEATURE:
<223> OTHER INFORMATION: Description of the artificial sequence:
      EcoRI cleavage site, T7 RNA Polymerase promoter

<400> SEQUENCE: 1
ggaattctaa tacgactcac tatagggcga tcagatctct agaag            45

<210> SEQ ID NO 2
<211> LENGTH: 50
<212> TYPE: DNA
<213> ORGANISM: Artificial Sequence
<220> FEATURE:
<223> OTHER INFORMATION: Description of the artificial sequence:
      BamHI cleavage site, SP6 RNA Polymerase promoter

<400> SEQUENCE: 2
```

```
gggatccatt taggtgacac tatagaatac ccatgatcgc gtagtcgata            50
```

<210> SEQ ID NO 3
<211> LENGTH: 340
<212> TYPE: RNA
<213> ORGANISM: Artificial Sequence
<220> FEATURE:
<223> OTHER INFORMATION: Description of the artificial sequence:
     RNA which corresponds to a sequence from the positive control DNA
     of the HeLa Nuclear Extract in vitro transcription kit from
     Promega

<400> SEQUENCE: 3

```
ucagaucucu agaagcuuua augcgguagu uuaucacagu uaaauugcua acgcagucag    60
gcaccgugua ugaaaucuaa caaugcgcuc aucgucaucc ucggcaccgu cacccuggau   120
gcuguaggca uaggcuuggu uaugccggua cugccgggcc ucuugcggga uaucguccau   180
uccgacagca ucgccaguca cuauggcgug cugcuagcgc uauaugcguu gaugcaauuu   240
cuaugcgcac ccguucucgg agcacugucc gaccgcuuug gccgccgccc aguccugcuc   300
gcuucgcuac uuggagccac uaucgacuac gcgaucaugg                        340
```

<210> SEQ ID NO 4
<211> LENGTH: 363
<212> TYPE: DNA
<213> ORGANISM: Artificial Sequence
<220> FEATURE:
<223> OTHER INFORMATION: Description of the artificial sequence:
     DNA which corresponds to a sequence from the positive control DNA
     of the HeLa Nuclear Extract in vitro transcription kit from
     Promega

<400> SEQUENCE: 4

```
tcagatctct agaagcttta atgcggtagt ttatcacagt taaattgcta acgcagtcag    60
gcaccgtgta tgaaatctaa caatgcgctc atcgtcatcc tcggcaccgt caccctggat   120
gctgtaggca taggcttggt tatgccggta ctgccgggcc tcttgcggga tatcgtccat   180
tccgacagca tcgccagtca ctatggcgtg ctgctagcgc tatatgcgtt gatgcaattt   240
ctatgcgcac ccgttctcgg agcactgtcc gaccgctttg gccgccgccc agtcctgctc   300
gcttcgctac ttggagccac tatcgactac gcgatcatgg cgaccacacc cgtcctgtgg   360
atc                                                                363
```

<210> SEQ ID NO 5
<211> LENGTH: 315
<212> TYPE: RNA
<213> ORGANISM: Artificial Sequence
<220> FEATURE:
<223> OTHER INFORMATION: Description of the artificial sequence:
     Sequence from the YFP gene

<400> SEQUENCE: 5

```
auggugagca agggcgagga gcuguucacc ggggugguge ccauccuggu cgagcuggac    60
ggcgacguaa acggccacaa guucagcgug uccggcgagg gcgagggcga ugccaccuac   120
ggcaagcuga cccugaaguu caucugcacc accggcaagc ugcccgugcc cuggcccacc   180
cucgugacca cccugaccua cggcgugcag ugcuucagcc gcuaccccga ccaugaag    240
cagcacgacu ucuucaaguc cgccaugccc gaaggcuacg uccaggagcg caccaucuuc   300
uucaaggacg acggc                                                   315
```

<210> SEQ ID NO 6

```
<211> LENGTH: 52
<212> TYPE: DNA
<213> ORGANISM: Artificial Sequence
<220> FEATURE:
<223> OTHER INFORMATION: Description of the artificial sequence:
      EcoRI cleavage site, T7 RNA Polymerase promoter, complementary
      region to the YFP gene

<400> SEQUENCE: 6
ggaattctaa tacgactcac tatagggcga atggtgagca agggcgagga gc          52

<210> SEQ ID NO 7
<211> LENGTH: 53
<212> TYPE: DNA
<213> ORGANISM: Artificial Sequence
<220> FEATURE:
<223> OTHER INFORMATION: Description of the artificial sequence:
      BamHI cleavage site, SP6 RNA Polymerase promoter, complementary
      region to the YFP gene

<400> SEQUENCE: 7
gggatccatt taggtgacac tatagaatac gccgtcgtcc ttgaagaaga tgg          53

<210> SEQ ID NO 8
<211> LENGTH: 21
<212> TYPE: RNA
<213> ORGANISM: Artificial Sequence
<220> FEATURE:
<223> OTHER INFORMATION: Description of the artificial sequence:
      RNA which corresponds to a sequence from the YFP gene

<400> SEQUENCE: 8
ucgagcugga cggcgacgua a                                             21
```

METHOD AND MEDICAMENT FOR INHIBITING THE EXPRESSION OF A GIVEN GENE

CROSS-REFERENCE TO RELATED APPLICATIONS

This application is a continuation of U.S. patent application Ser. No. 11/982,325, filed Oct. 31, 2007, which is a continuation of U.S. patent application Ser. No. 10/612,179, filed Jul. 2, 2003, now issued, which is a divisional of U.S. patent application Ser. No. 09/889,802, filed Sep. 17, 2001, now abandoned, which is the National Stage of International Patent Application No. PCT/DE00/00244, filed Jan. 29, 2000, which claims priority to German Patent Application No. DE19903713.2, filed Jan. 30, 1999, and German Patent Application No. DE19956568.6, filed Nov. 24, 1999. The contents of these prior applications are hereby incorporated by reference in their entirety for all purposes.

The invention relates to a medicament and to a use of double-stranded oligoribonucleotides and to a vector encoding them.

Such a method is known from WO 99/32619, which was unpublished at the priority date of the present invention. The known process aims at inhibiting the expression of genes in cells of invertebrates. To this end, the double-stranded oligoribonucleotide must exhibit a sequence which is identical with the target gene and which has a length of at least 50 bases. To achieve efficient inhibition, the identical sequence must be 300 to 1000 base pairs in length. Such an oligoribonucleotide is complicated to prepare.

DE 196 31 919 C2 describes an antisense RNA with specific secondary structures, the antisense RNA being present in the form of a vector encoding it. The antisense RNA takes the form of an RNA molecule which is complementary to regions of the mRNA. Inhibition of the gene expression is caused by binding to these regions. This inhibition can be employed in particular for the diagnosis and/or therapy of diseases, for example tumor diseases or viral infections.—The disadvantage is that the antisense RNA must be introduced into the cell in an amount which is at least as high as the amount of the mRNA. The known antisense methods are not particularly effective.

U.S. Pat. No. 5,712,257 discloses a medicament comprising mismatched double-stranded RNA (dsRNA) and bioactive mismatched fragments of dsRNA in the form of a ternary complex together with a surfactant. The dsRNA used for this purpose consists of synthetic nucleic acid single strands without defined base sequence. The single strands undergo irregular base pairing, also known as "non-Watson-Crick" base pairing, giving rise to mismatched double strands. The known dsRNA is used to inhibit the amplification of retroviruses such as HIV. Amplification of the virus can be inhibited when non-sequence-specific dsRNA is introduced into the cells. This leads to the induction of interferon, which is intended to inhibit viral amplification. The inhibitory effect, or the activity, of this method is poor.

It is known from Fire, A. et al., NATURE, Vol. 391, pp. 806 that dsRNA whose one strand is complementary in segments to a nematode gene to be inhibited inhibits the expression of this gene highly efficiently. It is believed that the particular activity of the dsRNA used in nematode cells is not due to the antisense principle but possibly on catalytic properties of the dsRNA, or enzymes induced by it.—Nothing is mentioned in this paper on the activity of specific dsRNA with regard to inhibiting the gene expression, in particular in mammalian and human cells.

The object of the present invention is to do away with the disadvantages of the prior art. In particular, it is intended to provide as effective as possible a method, medicament or use for the preparation of a medicament, which method, medicament or use is capable of causing particularly effective inhibition of the expression of a given target gene.

This object is achieved by the features of the claims presented here. Advantageous embodiments can be seen from the claims presented here.

In accordance with the method-oriented inventions, it is provided in each case that the region I which is complementary to the target gene exhibits not more than 49 successive nucleotide pairs.

Provided in accordance with the invention are an oligoribonucleotide or a vector encoding therefor. At least segments of the oligoribonucleotide exhibit a defined nucleotide sequence. The defined segment may be limited to the complementary region I. However, it is also possible that all of the double-stranded oligoribonucleotide exhibits a defined nucleotide sequence.

Surprisingly, it has emerged that an effective inhibition of the expression of the target gene can be achieved even when the complementary region I is not more than 49 base pairs in length. The procedure of providing such oligoribonucleotides is less complicated.

In particular, dsRNA with a length of over 50 nucleotide pairs induces certain cellular mechanisms, for example the dsRNA-dependent protein kinase or the 2-5A system, in mammalian and human cells. This leads to the disappearance of the interference effect mediated by the dsRNA which exhibits a defined sequence. As a consequence, protein biosynthesis in the cell is blocked. The present invention overcomes this disadvantage in particular.

Furthermore, the uptake of dsRNA with short chain lengths into the cell or into the nucleus is facilitated markedly over longer-chain dsRNAs.

It has proved advantageous for the dsRNA or the vector to be present packaged into micellar structures, preferably in liposomes. The dsRNA or the vector can likewise be enclosed in viral natural capsids or in chemically or enzymatically produced artificial capsids or structures derived therefrom. The abovementioned features make it possible to introduce the dsRNA or the vector into given target cells.

In a further aspect, the dsRNA has 10 to 1000, preferably 15 to 49, base pairs. Thus, the dsRNA can be longer than the region I, which is complementary to the target gene. The complementary region I can be located at the terminus or inserted into the dsRNA. Such dsRNA or a vector provided for coding the same can be produced synthetically or enzymatically by customary methods.

The gene to be inhibited is expediently expressed in eukaryotic cells. The target gene can be selected from the following group: oncogene, cytokin gene, Id protein gene, developmental gene, prion gene. It can also be expressed in pathogenic organisms, preferably in plasmodia. It can be part of a virus or viroid which is preferably pathogenic to humans.—The method proposed makes it possible to produce compositions for the therapy of genetically determined diseases, for example cancer, viral diseases or Alzheimer's disease.

The virus or viroid can also be a virus or viroid which is pathogenic to animals or plant-pathogenic. In this case, the method according to the invention also permits the provision of compositions for treating animal or plant diseases.

In a further aspect, segments of the dsRNA are designed as double-stranded. A region II which is complementary within the double-stranded structure is formed by two separate RNA single strands or by autocomplementary regions of a topologically closed RNA single strand which is preferably in circular form.

The ends of the dsRNA can be modified to counteract degradation in the cell or dissociation into the single strands. Dissociation takes place in particular when low concentrations or short chain lengths are used. To inhibit dissociation in a particularly effective fashion, the cohesion of the complementary region II, which is caused by the nucleotide pairs, can be increased by at least one, preferably two, further chemical linkage(s).—A dsRNA according to the invention whose dissociation is reduced exhibits greater stability to enzymatic and chemical degradation in the cell or in the organism.

The complementary region II can be formed by autocomplementary regions of an RNA hairpin loop, in particular when using a vector according to the invention. To afford protection from degradation, it is expedient for the nucleotides to be chemically modified in the loop region between the double-stranded structure.

The chemical linkage is expediently formed by a covalent or ionic bond, a hydrogen bond, hydrophobic interactions, preferably van-der-Waals or stacking interactions, or by metal-ion coordination. In an especially advantageous aspect, it can be formed at at least one, preferably both, end(s) of the complementary region II.

It has furthermore proved to be advantageous for the chemical linkage to be formed by one or more linkage groups, the linkage groups preferably being poly(oxyphosphinicooxy-1,3-propanediol) and/or poly-ethylene glycol chains. The chemical linkage can also be formed by purine analogs used in place of purines in the complementary regions II. It is also advantageous for the chemical linkage to be formed by azabenzene units introduced into the complementary regions II. Moreover, it can be formed by branched nucleotide analogs used in place of nucleotides in the complementary regions II.

It has proved expedient to use at least one of the following groups for generating the chemical linkage: methylene blue; bifunctional groups, preferably bis(2-chloroethyl)amine; N-acetyl-N'-(p-glyoxyl-benzoyl)cystamine; 4-thiouracil; psoralene. The chemical linkage, can furthermore be formed by thiophosphoryl groups provided at the ends of the double-stranded region. The chemical linkage at the ends of the double-stranded region is preferably formed by triple-helix bonds.

The chemical linkage can expediently be induced by ultraviolet light.

The nucleotides of the dsRNA can be modified. This counteracts the activation, in the cell, of a double-stranded-RNA-dependent protein kinase, PKR. Advantageously, at least one 2'-hydroxyl group of the nucleotides of the dsRNA in the complementary region II is replaced by a chemical group, preferably a 2'-amino or a 2'-methyl group. At least one nucleotide in at least one strand of the complementary region II can also be a locked nucleotide with a sugar ring which is chemically modified, preferably by a 2'-O, 4'-C methylene bridge. Advantageously, several nucleotides are locked nucleotides.

A further especially advantageous embodiment provides that the dsRNA or the vector is bound to, associated with or surrounded by, at least one viral coat protein which originates from a virus, is derived therefrom or has been prepared synthetically. The coat protein can be derived from polyomavirus. The coat protein can contain the polyomavirus virus protein 1 (VP1) and/or virus protein 2 (VP2). The use of such coat proteins is known from, for example, DE 196 18 797 A1, whose disclosure is herewith incorporated.—The abovementioned features considerably facilitate the introduction of the dsRNA or of the vector into the cell.

When a capsid or capsid-type structure is formed from the coat protein, one side preferably faces the interior of the capsid or capsid-type structure. The construct formed is particularly stable.

The dsRNA can be complementary to the primary or processed RNA transcript of the target gene.—The cell can be a vertebrate cell or a human cell.

At least two dsRNAs which differ from each other or at least one vector encoding them can be introduced into the cell, where at least segments of one strand of each dsRNA are complementary to in each case one of at least two different target genes. This makes it possible simultaneously to inhibit the expression of at least two different target genes. In order to suppress, in the cell, the expression of a double-stranded-RNA-dependent protein kinase, PKR, one of the target genes is advantageously the PKR gene. This allows effective suppression of the PKR activity in the cell.

The invention furthermore provides a medicament with at least one oligoribonucleotide with double-stranded structure (dsRNA) for inhibiting the expression of a given target gene, where one strand of the dsRNA has a region I where at least segments are complementary to the target gene.—Surprisingly, it has emerged that such a dsRNA is suitable as medicament for inhibiting the expression of a given gene in mammalian cells. In comparison with the use of single-stranded oligoribonucleotides, the inhibition is already caused at concentrations which are lower by at least one order of magnitude. The medicament according to the invention is highly effective. Lesser side effects can be expected.

The invention furthermore provides a medicament with at least one vector for coding at least one oligoribonucleotide with double-stranded structure (dsRNA) for inhibiting the expression of a given target gene, where one strand of the dsRNA has a region I where at least segments are complementary to the target gene.—The medicament proposed exhibits the abovementioned advantages. By, using a vector, in particular production costs can be reduced.

In a particularly advantageous embodiment, the complementary region I has not more than 49 successive nucleotide pairs.—Surprisingly, it has emerged that an effective inhibition of the expression of the target gene can be achieved even when the complementary region I is not more than 49 base pairs in length. The procedure of providing such oligoribonucleotides is less complicated.

The invention furthermore provides a use of an oligoribonucleotide with double-stranded structure (dsRNA) for preparing a medicament for inhibiting the expression of a given target gene, where one strand of the dsRNA has a region I where at least segments are complementary to the target gene.—Surprisingly, such a dsRNA is suitable for preparing a medicament for inhibiting the expression of a given gene. Compared with the use of single-stranded oligoribonucleotides, the inhibition is already caused at concentrations which are lower by one order of magnitude when using dsRNA. The use according to the invention thus makes possible the preparation of particularly effective medicaments.

The invention furthermore provides the use of a vector for coding at least one oligoribonucleotide with double-stranded structure (dsRNA) for preparing a medicament for inhibiting the expression of a given target gene, where one strand of the dsRNA has a region I where at least segments are complementary to this target gene.—The use of a vector makes possible a particularly effective gene therapy.

With regard to advantageous embodiments of the medicament and of the use, reference is made to the description of the above features.

Figure 2:
Figure 3:
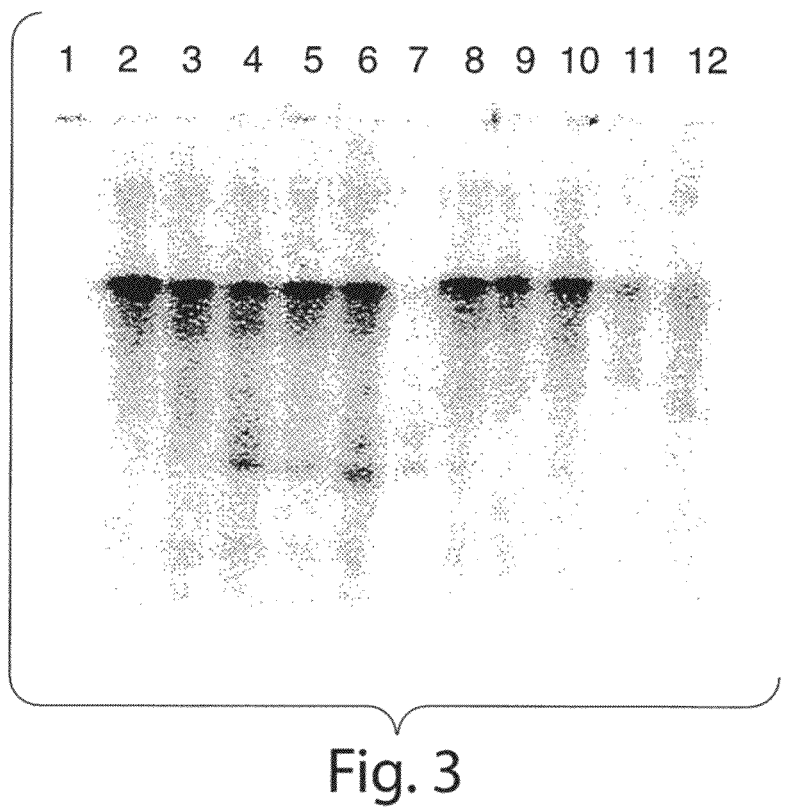

Use examples of the invention are illustrated in greater detail hereinbelow with reference to the figures, in which:

FIG. 1 shows the schematic representation of a plasmid for the in vitro, transcription with T7- and SP6-polymerase, FIG. 2 shows RNA following electrophoresis on an 8% polyacrylamide gel and staining with ethidium bromide, FIG. 3 shows a representation of radioactive RNA transcripts following electrophoresis on an 8% polyacrylamide gel with 7 M urea by means of an instant imager, and FIGS. 4a-e show Texas Red and YFP fluorescence in murine fibroblasts.

USE EXAMPLE 1

The inhibition of transcription was detected by means of sequence homologous dsRNA in an in vitro transcription system with a nuclear extract from human HeLa cells. The DNA template for this experiment was plasmid pCMV 1200 which had been linearized by means of BamHI.

Generation of the Template Plasmids:

The plasmid shown in FIG. 1 was constructed for use in the enzymatic synthesis of the dsRNA. To this end, a polymerase chain reaction (PCR) with the "positive control DNA" of the HelaScribe® Nuclear Extract in vitro transcription kit by Promega, Madison, USA, as DNA template was first carried out. One of the primers used contained the sequence of an EcoRI cleavage site and of the T7 RNA polymerase promoter as shown in sequence listing No. 1. The other primer contained the sequence of a BamHI cleavage site and of the SP6 RNA polymerase promoter as shown in sequence listing No. 2. In addition, the two primers had, at the 3' ends, regions which were identical with or complementary to the DNA template. The PCR was carried out by means of the "Taq PCR Core Kits" by Qiagen, Hilden, Germany, following the manufacturer's instructions. 1.5 mM $MgCl_2$, in each case 200 µM dNTP, in each case 0.5 µM primer, 2.5 U Taq DNA polymerase and approximately 100 ng of "positive control DNA" were employed as template in PCR buffer in a volume of 100 µl. After initial denaturation of the template DNA by heating for 5 minutes at 94° C., amplification was carried out in 30 cycles of denaturation for in each case 60 seconds at 94° C., annealing for 60 seconds at 5° C. below the calculated melting point of the primers and polymerization for 1.5-2 minutes at 72° C. After a final polymerization of 5 minutes at 72° C., 5 µl of the reaction were analyzed by agarose-gel electrophoresis. The length of the DNA fragment amplified thus was 400 base pairs, 340 base pairs corresponding to the "positive control DNA". The PCR product was purified, hydrolyzed with EcoRI and BamHI and, after repurification, employed in the ligation together with a pUC18 vector which had also been hydrolyzed by EcoRI and BamHI. *E. coli* XL1-blue was then transformed. The plasmid obtained (pCMV5) carries a DNA fragment whose 5' end is flanked by the T7 promoter and whose 3' end is flanked by the SP6 promoter. By linearizing the plasmid with BamHI, it can be employed in vitro with the T7-RNA polymerase for the run-off transcription of a single-stranded RNA which is 340 nucleotides in length and shown in sequence listing No. 3. If the plasmid is linearized with EcoRI, it can be employed for the run-off transcription with SP6 RNA polymerase, giving rise to the complementary strand. In accordance with the method outlined hereinabove, an RNA 23 nucleotides in length was also synthesized. To this end, a DNA shown in sequence listing No. 4 was ligated with the pUC18 vector via the EcoRI and BamHI cleavage sites.

Plasmid pCMV 1200 was constructed as DNA template for the in-vitro transcription with HeLa nuclear extract. To this end, a 1 191 bp EcoRI/BamHI fragment of the positive control DNA contained in the HeLaScribe® Nuclear Extract in vitro transcription kit was amplified by means of PCR. The amplified fragment encompasses the 828 bp "immediate early" CMV promoter and a 363 bp transcribable DNA fragment. The PCR product was ligated to the vector pGEM-T via "T-overhang" ligation. A BamHI cleavage site is located at the 5' end of the fragment. The plasmid was linearized by hydrolysis with BamHI and used as template in the run-off transcription.

In-Vitro Transcription of the Complementary Single Strands:

pCMV5 plasmid DNA was linearized with EcoRI or BamHI. It was used as DNA template for an in-vitro transcription of the complementary RNA single strands with SP6 and T7 RNA polymerase, respectively. The "Riboprobe in vitro Transcription" system by Promega, Madison, USA, was employed for this purpose. Following the manufacturer's instructions, 2 µg of linearized plasmid DNA were incubated in 100 µl of transcription buffer and 40 U T7 or SP6 RNA polymerase for 5-6 hours at 37° C. The DNA template was subsequently degraded by addition of 2.5 µl of RNase-free DNase RQ1 and incubation for 30 minutes at 37° C. The transcription reaction was made up to 300 µl with $H_2O$ and purified by phenol extraction. The RNA was precipitated by addition of 150 µl of 7 M ammonium acatate [sic] and 1 125 µl of ethanol and stored at −65° C. until used for the hybridization.

Generation of the RNA Double Strands:

For the hybridization, 500 µl of the single-stranded RNA which had been stored in ethanol and precipitated were spun down. The resulting pellet was dried and taken up in 30 µl of PIPES buffer, pH 6.4 in the presence of 80% formamide, 400 mM NaCl and 1 mM EDTA. In each case 15 µl of the complementary single strands were combined and heated for 10 minutes at 85° C. The reactions were subsequently incubated overnight at 50° C. and cooled to room temperature.

Only approximately equimolar amounts of the two single strands were employed in the hybridization. This is why the dsRNA preparations contained single-stranded RNA (ssRNA) as contaminant. In order to remove these ssRNA contaminants, the reactions were treated, after hybridization, with the single-strand-specific ribonucleases bovine pancreatic RNase A and *Aspergillus oryzae* RNase T1. RNase A is an endoribonuclease which is specific for pyrimidines. RNase T1 is an endoribonuclease which preferentially cleaves at the 3' side of guanosines. dsRNA is no substrate for these ribonucleases. For the RNase treatment, the reactions in 300 µl of Tris, pH 7.4, 300 mM NaCl and 5 mM EDTA were treated with 1.2 µl of RNaseA at a concentration of 10 mg/ml and 2 µl of RNaSeT1 at a concentration of 290 µg/ml. The reactions were incubated for 1.5 hours at 30° C. Thereupon, the RNases were denatured by addition of 5 µl of proteinase K at a concentration of 20 mg/ml and 10 µl of 20% SDS and incubation for 30 minutes at 37° C. The dSRNA was purified by phenol extraction and precipitated with ethanol. To verify the completeness of the RNase digestion, two control reactions were treated with ssRNA analogously to the hybridization reactions.

The dried pellet was taken up in 15 µl of TE buffer, pH 6.5, and subjected to native polyacrylamide gel electrophoresis on an 8% gel. The acrylamide gel was subsequently stained in an ethidium bromide solution and washed in a water bath. FIG. 2 shows the RNA which had been visualized in a UV transilluminator. The sense RNA which had been applied to lane 1 and the antisense RNA which had been applied to lane 2 showed a different migration behavior under the chosen conditions than the dsRNA of the hybridization reaction which had been applied to lane 3. The RNase-treated sense RNA and antisense RNA which had been applied to lanes 4 and 5, respectively, produced no visible band. This shows that the single-stranded RNAs had been degraded completely. The RNase-treated dsRNA of the hybridization reaction which had been applied to lane 6 is resistant to RNase treatment. The band which migrates faster in the native gel in comparison with the dsRNA applied to lane 3 results from dsRNA which is free from ssRNA. In addition to the dominant main band, weaker bands which migrate faster are observed after the RNase treatment.

In-Vitro Transcription Test with Human Nuclear Extract:

Using the HeLaScribe® Nuclear Extract in vitro transcription kit by Promega, Madison, USA, the transcription efficiency of the abovementioned DNA fragment which is present in plasmid pCMV 1200 and homologous to the "positive control DNA" was determined in the presence of the dsRNA (dsRNA-CMV5) with sequence homology. Also, the effect of the dsRNA without sequence homology, which corresponds to the yellow fluorescent protein (YFP) gene (dsRNA-YRP), was studied. This dsRNA had been generated analogously to the dsRNA with sequence homology. The sequence of a strand of this dsRNA can be found in sequence listing No. 5. Plasmid pCMV 1200 was used as template for the run-off transcription. It carries the "immediate early" cytomegalovirus promoter which is recognized by the eukaryotic RNA polymerase II, and a transcribable DNA fragment. Transcription was carried out by means of the HeLa nuclear extract, which contains all the proteins which are necessary for transcription. By addition of [•-$^{32}$P] rGTP to the transcription reaction, radiolabeled transcript was obtained. The [•-$^{32}$P] rGTP used had a specific activity of 400 Ci/mmol, 10 mCi/ml. 3 mM MgCl$_2$, in each case 400 µM rATP, rCTP, rUTP, 16 µM rGTP, 0.4 µM [•-$^{32}$P] rGTP and depending on the experiment 1 fmol of linearized plasmid DNA and various amounts of dsRNA in transcription buffer were employed per reaction. Each batch was made up to a volume of 8.5 µl with H$_2$O. The reactions were mixed carefully. To start the transcription, 4 U HeLa nuclear extract in a volume of 4 µl were added and incubated for 60 minutes at 30° C. The reaction was stopped by addition of 87.5 µl of quench mix which had been warmed to 30° C. To remove the proteins, the reactions were treated with 100 µl of phenol/chloroform/isoamyl alcohol (25:24:1 v/v/v) saturated with TE buffer, pH 5.0, and the reactions were mixed vigorously for 1 minute. For phase separation, the reactions were spun for approximately 1 minute at 12 000 rpm and the top phase was transferred into a fresh reaction vessel. Each reaction was treated with 250 µl of ethanol. The reactions were mixed thoroughly and incubated for at least 15 minutes on dry ice/methanol. To precipitate the RNA, the reactions were spun for 20 minutes at 12 000 rpm and 40° C. The supernatant was discarded. The pellet was dried in vacuo for 15 minutes and resuspended in 10 µl of H$_2$O. Each reaction was treated with 10 µl of denaturing loading buffer. The free GTP was separated from the transcript formed by means of denaturing polyacrylamide gel electrophoresis on an 8% gel with 7 M urea. The RNA transcripts formed upon transcription with HeLa nuclear extract, in denaturing loading buffer, were heated for 10 minutes at 90° C. and 10 µl aliquots were applied immediately to the freshly washed pockets. The electrophoresis was run at 40 mA. The amount of the radioactive ssRNA formed upon transcription was analyzed after electrophoresis with the aid of an Instant Imager.

FIG. 3 shows the radioactive RNA from a representative test, shown by means of the Instant Imager. Samples obtained from the following transcription reactions were applied:
Lane 1: without template DNA, without dsRNA;
Lane 1: 50 ng of template DNA, without dsRNA;
Lane 3: 50 ng of template DNA, 0.5 µg of dsRNA YFP;
Lane 4: 50 ng of template DNA, 1.5 µg of dsRNA YFP;
Lane 5: 50 ng of template DNA, 3 µg of dsRNA: YFP;
Land 6: 50 ng of template DNA, 5 µg of dsRNA YFP;
Lane 7: without template DNA, 1.5 dsRNA YFP;
Lane 8: 50 ng of template DNA, without dsRNA;
Lane 9: 50 ng of template DNA, 0.5 µg of dsRNA CMV5;
Lane 10: 50 ng of template DNA, 1.5 µg of dsRNA CMV5;
Lane 11: 50 ng of template DNA, 3 µg of dsRNA CMV5;
Lane 12: 50 ng of template DNA, 5 µg of dsRNA CMV5;

It emerged that the amount of transcript was reduced markedly in the presence of dsRNA with sequence homology in comparison with the control reaction without dsRNA and with the reactions with dsRNA YFP without sequence homology. The positive control in lane 2 shows that radioactive transcript was formed upon the in-vitro transcription with HeLa nuclear extract. The reaction is used for comparison with the transcription reactions which had been incubated in the presence of dsRNA. Lanes 3 to 6 show that the addition of non-sequentially-specific dsRNA YFP had no effect on the amount of transcript formed. Lanes 9 to 12 show that the addition of an amount of between 1.5 and 3 µg of sequentially-specific dsRNA CMV5 leads to a reduction in the amount of transcript formed. In order to exclude that the effects observed are based not on the dsRNA but on any contamination which might have been carried along accidentally during the preparation of the dsRNA, a further control was carried out. Single-stranded RNA was transcribed as described above and subsequently subjected to the RNase treatment. It was demonstrated by means of native polyacrylamide gel electrophoresis that the ssRNA had been degraded completely. This reaction was subjected to phenol extraction and ethanol precipitation and subsequently taken up in PE buffer, as were the hybridization reactions. This gave a sample which contained no RNA but had been treated with the same enzymes and buffers as the dsRNA. Lane 8 shows that the addition of this sample had no effect on transcription. The reduction of the transcript upon addition of sequence-specific dsRNA can therefore be ascribed unequivocally to the dsRNA itself. The reduction of the amount of transcript of a gene in the presence of dsRNA in a human transcription system indicates an inhibition of the expression of the gene in question. This effect can be attributed to a novel mechanism caused by the dsRNA.

USE EXAMPLE 2

The test system used for these in-vivo experiments was the murine fibroblast cell line NIH3T3, ATCC CRL-1658. The YFP gene was introduced into the nuclei with the aid of microinjection. Expression of YFP was studied under the effect of simultaneously cotransfected dsRNA with sequence homology. This dsRNA YFP shows homology with the 5'-region of the YFP gene over a length of 315 bp. The nucleotide sequence of a strand of the dsRNA YRP is shown in sequence listing No. 5. Evaluation under the fluorescence microscope was carried out 3 hours after injection with reference to the greenish-yellow fluorescence of the YFP formed.

Construction of the Template Plasmid, and Preparation of the dsRNA:

A plasmid was constructed following the same principle as described in use example 1 to act as template for the production of the YFP dsRNA by means of T7 and SP6 in-vitro transcription. Using the primer Eco_T7_YFP as shown in sequence listing No. 6 and Bam_SP6_YFP as shown in sequence listing No. 7, the desired gene fragment was amplified by PCR and used analogously to the above description for preparing the dsRNA. The dsRNA YFP obtained is identical to the dsRNA used in use example 1 as non-sequence-specific control.

A dsRNA linked chemically at the 3' end of the RNA as shown in sequence listing No. 8 to the 5' end of the complementary RNA via a C18 linker group was prepared (L-dsRNA). To this end, synthons modified by disulfide bridges were used. The 3'-terminal synthon is bound to the solid support via the 3' carbon with an aliphatic linker group via a disulfide bridge. In the 5'-terminal synthon of the complementary oligoribonucleotide which is complementary to the 3'-terminal synthon of the one oligoribonucleotide, the 5'-trityl protecting group is bound via a further aliphatic linker and a disulfide bridge. Following synthesis of the two single strands, removal of the protecting groups and hybridization of the complementary oligoribonucleotides, the thiol groups which form are brought into spatial vicinity. The single strands are linked to each other by oxidation via their aliphatic linkers and a disulfide bridge. This is followed by purification with the aid of HPLC.

Preparation of the Cell Cultures:

The cells were incubated in DMEM supplemented with 4.5 g/l glucose, 10% fetal bovine serum in culture dishes at 37° C. under a 7.5% $CO_2$ atmosphere and passaged before reaching confluence. The cells were detached with trypsin/EDTA. To prepare for microinjection, the cells were transferred into Petri dishes and incubated further until microcolonies formed.

Microinjection:

For the microinjection, the culture dishes were removed from the incubator for approximately 10 minutes. Approximately 50 nuclei were injected singly per reaction within a marked area using the AIS microinjection system from Carl Zeiss, Göttingen, Germany. The cells were subsequently incubated for three more hours. For the microinjection, borosilicate glass capillaries from Hilgenberg GmbH, Malsfeld, Germany, with a diameter of less than 0.5 µm at the tip were prepared. The microinjection was carried out using a micromanipulator from Narishige Scientific Instrument Lab., Tokyo, Japan. The injection time was 0.8 seconds and the pressure was approximately 100 hPa. The transfection was carried out using the plasmid pCDNA YFP, which contains an approximately 800 bP BamHI/EcoRI fragment with the YFP gene in vector pcDNA3. The samples injected into the nuclei contained 0.01 µg/µl of pCDNA-YFP and Texas Red coupled to dextran-70000 in 14 mM NaCl, 3 mM KCl, 10 mM $KPO_4$ [sic], ph 7.5. Approximately 100 pl of RNA with a concentration of 1 µM or, in the case of the L-dsRNA, 375 µM were additionally added.

The cells were studied under a fluorescence microscope with excitation with the light of the excitation wavelength of Texas Red, 568 nm, or of YFP, 488 nm. Individual cells were documented by means of a digital carvers. FIGS. 4a-e show the result for NIH3T3 cells. In the cells shown in FIG. 4a, sense-YFP-ssRNA has been injected, in FIG. 4b antisense-YFP-ssRNA, in FIG. 4c dsRNA-YFP, in FIG. 4d no RNA and in FIG. 4e L-dsRNA.

The field on the left shows in each case the fluorescence of cells with excitation at 568 nm. The fluorescence of the same cells at an excitation of 488 nm is seen on the right. The Texas Red fluorescence of all the cells shown demonstrates that the injection solution had been applied successfully into the nuclei and that cells with successful hits were still alive after three hours. Dead cells no longer showed Texas Red fluorescence.

Figure 4A:
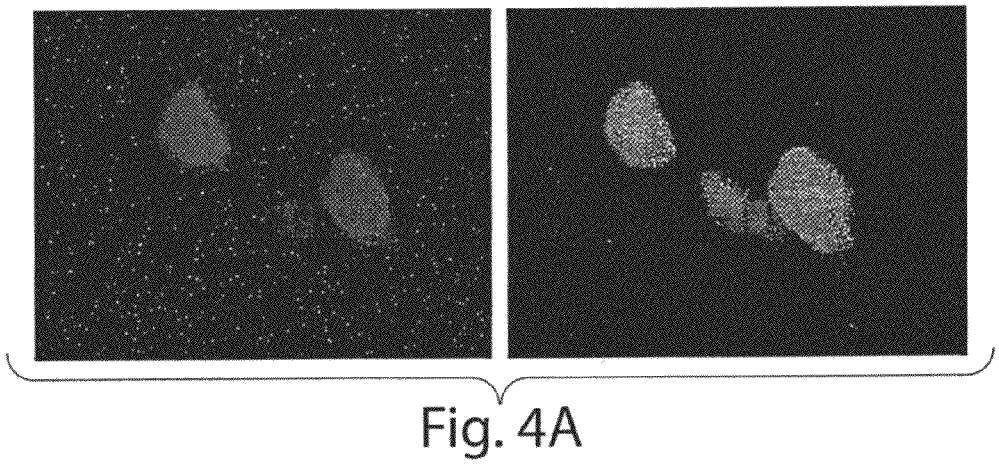
Figure 4B:
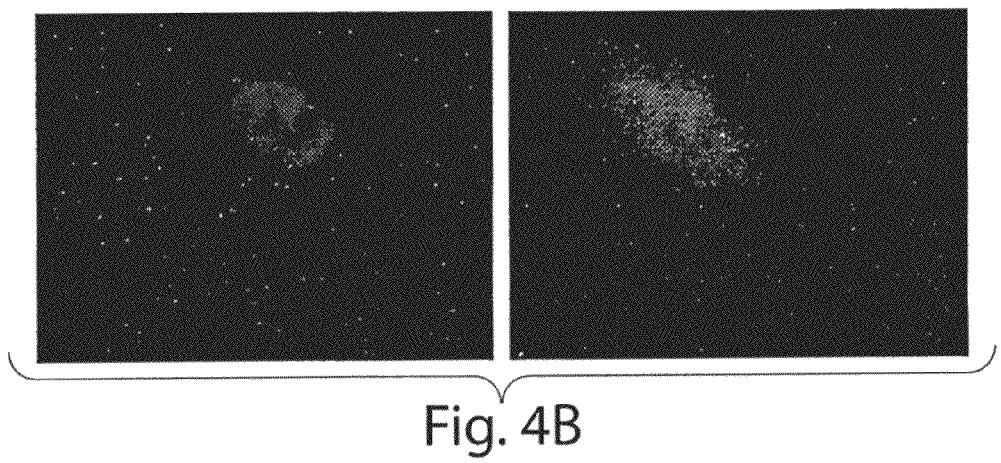
Figure 4C:
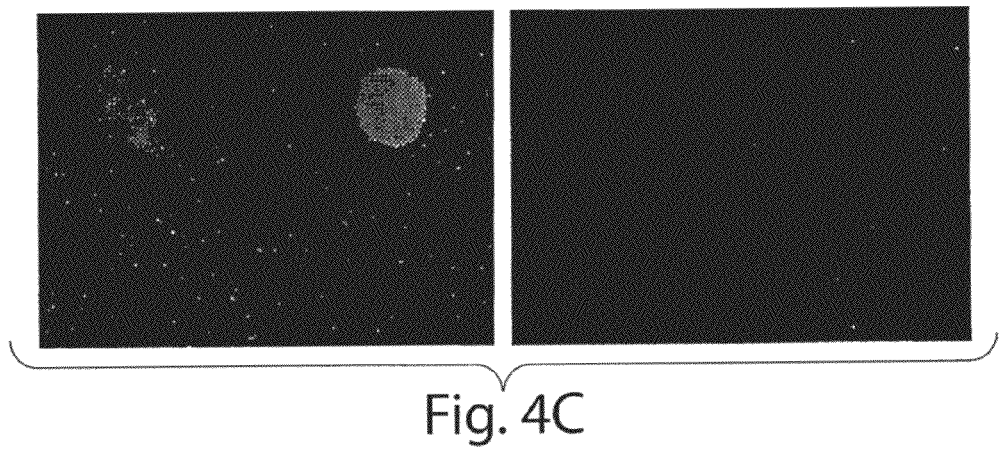
Figure 4D:
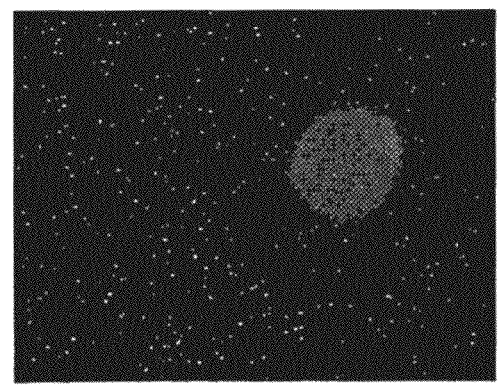
Figure 4D:
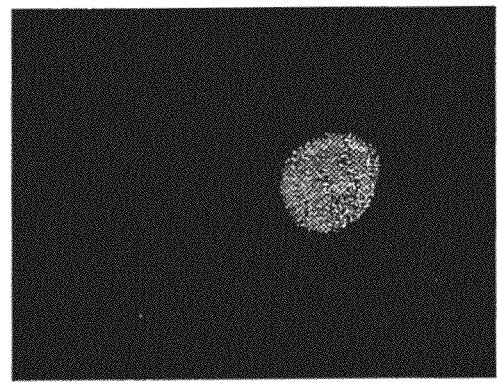
Figure 4E:
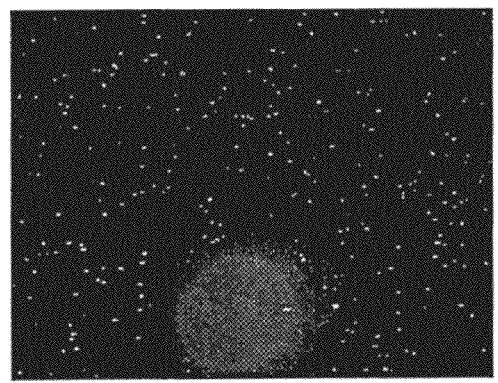
Figure 4E:
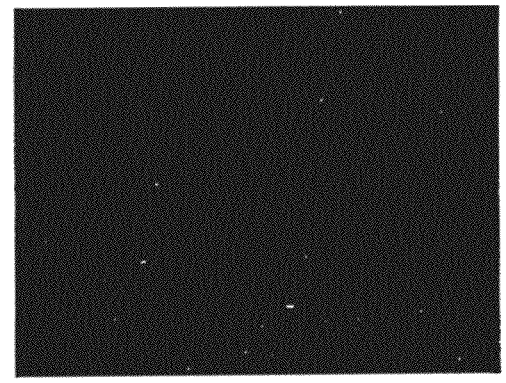

The right fields of each of FIGS. 4a and 4b show that YFP expression was not visibly inhibited when the single-stranded RNA was injected into the nuclei. The right field of FIG. 4c shows cells whose YFP fluorescence was no longer detectable after the injection of dsRNA-YFP. FIG. 4d shows cells into which no RNA had been injected, as control. The cell shown in FIG. 4e shows YFP fluorescence which can no longer be detected owing to the injection of the L-dsRNA which shows regions with sequence homology to the YFP gene. This result demonstrates that even shorter dsRNAs can be used for specifically inhibiting gene expression in mammals when the double strands are stabilized by chemically linking the single strands.

The invention claimed is:

1. An oligoribonucleotide of double-stranded structure (dsRNA) for inhibiting the expression of a given target gene in mammalian cells, wherein at least one strand of the dsRNA comprises a locked nucleotide, wherein at least one strand of the dsRNA comprises at least one chemically modified nucleotide that is distinct from the locked nucleotide, and wherein the dsRNA has 15 to 49 base pairs and has a complementary region I that is incorporated in the dsRNA.

2. The dsRNA of claim 1, wherein the complementary region I has not more than 49 nucleotide pairs.

3. The dsRNA of claim 1, wherein the chemically modified nucleotide is a 2'-modified nucleotide.

4. The dsRNA of claim 3, wherein the 2'-modified nucleotide is a 2'-methyl substituted nucleotide.

5. The dsRNA of claim 3, wherein the 2'-modified nucleotide is a 2'-amino substituted nucleotide.

6. The dsRNA of claim 1, wherein the locked nucleotide is chemically modified by a 2'-O,4'-C methylene bridge.

7. The dsRNA of claim 1, wherein the target gene is a mammalian gene or a viral gene.

8. The dsRNA of claim 1, wherein the target gene is selected from the group consisting of an oncogene, a cytokine gene, an Id protein gene, a developmental gene, a PKR gene and a prion gene.

9. The dsRNA of claim 1, wherein the dsRNA is enclosed by a micellar structure.

10. The dsRNA of claim 9, wherein the micellar structure comprises a liposome.

11. The dsRNA of claim 1, wherein the target gene is expressed in eukaryotic cells.

12. The dsRNA of claim 1, wherein an end of the dsRNA is modified in order for the double-stranded structure to counteract degradation.

13. The dsRNA of claim 1, wherein the dsRNA comprises a sense strand and an antisense strand, and wherein the sense strand comprises a 2'-methyl substituted nucleotide.

14. The dsRNA of claim 1, wherein the dsRNA comprises a sense strand and an antisense strand, and wherein the sense strand comprises a 2'-methoxynucleotide.

15. The dsRNA of claim 1, wherein the dsRNA comprises a sense strand and an antisense strand, and wherein the sense strand comprises a plurality of 2'-methoxynucleotides.

16. The dsRNA of claim 1, wherein the dsRNA comprises a pharmaceutical composition formulated for delivery to a mammalian cell.

17. A pharmaceutical composition comprising an oligoribonucleotide of double-stranded structure (dsRNA) for inhibiting the expression of a given target gene in mammalian cells, wherein at least one strand of the dsRNA comprises a locked nucleotide, wherein at least one strand of the dsRNA comprises at least one chemically modified nucleotide that is distinct from the locked nucleotide, and wherein the dsRNA has 15 to 49 base pairs and has a complementary region I that is incorporated in the dsRNA.

18. The pharmaceutical composition of claim 17, further comprising a liposome enclosing the dsRNA for delivery to a mammalian cell.

* * * * *